United States Patent [19]  
Neeser

[11] Patent Number: 4,994,441  
[45] Date of Patent: Feb. 19, 1991

[54] DENTAL ANTI-PLAQUE AND ANTI-CARIES AGENT

[75] Inventor: Jean-Richard Neeser, Lausanne, Switzerland

[73] Assignee: Nestec S.A., Vevey, Switzerland

[21] Appl. No.: 154,077

[22] Filed: Feb. 8, 1988

[30] Foreign Application Priority Data

Feb. 26, 1987 [CH] Switzerland .............. 732/87

[51] Int. Cl.$^5$ .............. A61K 37/02; A61K 7/16; A61K 9/20; A61K 9/68
[52] U.S. Cl. .............. 514/8; 514/775; 514/835; 514/900; 514/901; 514/959; 424/48; 424/49; 424/401; 424/464
[58] Field of Search .............. 530/322, 395, 344, 412, 530/833; 514/8, 775, 835, 844, 901, 900, 959; 424/48, 464, 49, 401; 426/3

[56] References Cited

U.S. PATENT DOCUMENTS

| 4,042,575 | 8/1977 | Eustache | 530/322 |
| 4,042,576 | 8/1977 | Eustache | 530/322 |
| 4,151,271 | 4/1979 | Dyroff et al. | 424/48 |
| 4,309,339 | 1/1982 | Haupt et al. | 530/412 |
| 4,485,040 | 11/1984 | Roger et al. | 530/833 |
| 4,495,176 | 1/1985 | Brule et al. | 424/131 |
| 4,579,736 | 4/1986 | Hammond | 424/195.1 |

OTHER PUBLICATIONS

Jolles et al., Chem. Abstr., vol. 79, No. 39452e (1973).
Mercier et al., Chem Abstr., vol. 86, No. 135209w (1977).
Pearce Chem. Abstr., vol. 93, No. 44093g (1980).
Neeser et al., Chem. Abstr., vol. 110, No. 72413z (1989).
Neeser, et al., Specific and Non specific Inhibition of Adhesion of Oral Actinomyces and Streptococci to Erythrocytes and Polystyrene by Caseinoglycopeptide Derivatives, Infection and Immunity, Dec. 1988, pp. 3201–3208, vol. 56, No. 12.
Brennan, et al., Lectin-Dependent Attachment of Actinomyces Raeslundiito Receptors of Epithelial Cells, Infect Immun., pp. 459–464, 1984.
Kolenbrander, Isolation and Characterization of Coaggregation-Defective Mutants of Actinomyces Viscosus, Actinomyces Naeslundii, & Steptococcus Sanguis. Infect Immun. 3:1, pp. 1200–1208, 9/1982.

Primary Examiner—John Doll
Assistant Examiner—Christina Chan
Attorney, Agent, or Firm—Vogt & O'Donnell

[57] ABSTRACT

Adhesion of bacteria in the buccal cavity which are responsible for the formation of dental plaque and caries is inhibited by kappa-caseino-glycopeptide compounds and desialylated derivatives thereof contained in compositions having a form suitable for being empolyed for treating the bacteria in the buccal cavity.

6 Claims, No Drawings

DENTAL ANTI-PLAQUE AND ANTI-CARIES AGENT

BACKGROUND OF THE INVENTION

This invention is concerned with inhibiting the adhesion of the bacteria responsible for dental plaque and caries.

*Actinomyces viscosus* and *Streptococcus sanguis* are bacteria populating the buccal cavity which are responsible for the initiation and formation of dental plaque. With *Actinomyces naeslundii*, they form a group of bacteria which are capable of colonizing above all the buccal cavity. They play a leading part in the sequence of events leading to the diseases associated with dental plaque, such as root caries, gingivitis, periodontitis and paradontolysis. In addition, *Streptococcus mutans* is the principal pathogen associated with dental caries which grows once dental plaque has started.

Among the factors entering into the mechanisms by which dental plaque is formed by the strains *A. viscosus* and *S. sanguis*, mention should be made of their properties of adhering to the buccal epithelial cells, to the surface of teeth coated with saliva and their tendency to form coaggregates with one another and with *A. naeslundii*. Although these mechanisms are extremely complex, it has been found that *A. naeslundii* recognizes a receptor containing galactose or galactosamine on the epithelial cells through adhesines likewise expressed by *A. viscosus* and termed type 2 pili. Other works have shown that the co-aggregation reactions between *S. sanguis* and these two *Actinomyces* species could also be based on the recognition of type 2 pili/galactose.

In simple terms, it would appear on the one hand that, in the prior art, the conventional inhibitor of bacterial adhesion governed by type 2pili is lactose acting through its galactose moiety. On the other hand, adhesion mechanisms based on other factors, for example bringing the solid surface of teeth into play, are instrumental in the formation of dental plaque.

US-PS 4,579,736 relates to the preparation of a factor for inhibiting the growth and the metabolism of the bacteria responsible for forming dental plaque, *S. sanguis* and *A. viscosus*, comprising breaking up the cell walls of *Actinobacillus actinomycetemcomitans* (which is a bacterium present in the final phase of periodontitis) by an ultrasonic treatment and collecting the factor in question by centrifugation and decantation of the supernatant liquid phase, purification thereof by dialysis and drying by freeze-drying. Published European patent application 184,121 relates to a dental-care additive which is intended to be incorporated in foods and medicaments containing sucrose and which consists essentially of a mixture of lactose and galactose obtained by fermentation of whey with *Lactobacillus leichmannii*.

SUMMARY OF THE INVENTION

We have found that glycopeptides of lactic origin show remarkable activity in inhibiting hemagglutinations governed by type 2 pili on the one hand and the adhesion of *A. viscosus*, *S. sanguis* and *S. mutans* to the surface of plastic materials on the other hand, their activity in this regard being clearly superior to that observed for lactose or galactose.

The present invention relates to a dental anti-plaque and anti-caries agent, characterized in that it consists essentially of an active principle selected from kappa-caseino-glycopeptides and desialylated derivatives thereof.

According to the invention, kappa-caseino-glycopeptides are understood to be both a caseino-macroglycopeptide, which is the water-soluble component emanating from the hydrolysis of kappa-casein by rennet, and a caseino-glycopeptide obtained by proteolysis of this caseino-macroglycopeptide.

Desialylated derivatives are understood to be the derivatives obtained from the above glycopeptides by more or less complete elimination of the sialic acids, i.e. N-acetylneuraminic and N-glycollylneuraminic acids, from the oligosaccharide chains.

DETAILED DESCRIPTION OF THE INVENTION

One preferred group of active principles is formed by kappa-caseino-macropeptides and desialylated derivatives thereof which show higher activity than the corresponding compounds which have been subjected to proteolysis.

One such agent may be prepared by reaction of a starting material of lactic origin, which has been hydrolyzed with rennet, with trichloroacetic acid to form a precipitate and a supernatant phase, separating the supernatant phase, subjecting it to dialysis, optionally purifying the dialyzed supernatant phase by gel filtration and drying the filtered product.

Suitable starting materials of lactic origin include:

the product of the hydrolysis with rennet of a native casein obtained by acidic precipitation of skimmed milk with a mineral acid or acidifying ferments, optionally with addition of calcium ions;

the hydrolysis product of a caseinate with rennet;

a sweet whey (obtained after separation of casein coagulated with rennet);

a sweet whey demineralized, for example, by electrodialysis and/or ion exchange and/or reverse osmosis, and freed from lactose to a greater or lesser extent; and a concentrate of whey proteins obtained by ultrafiltration and diafiltration (ultrafiltration with washing) of sweet whey, this particular starting material being preferred.

It is possible to use the above dairy products obtained from the milk of any milk-bearing female animals, preferably cows, goats or sheep.

The desialylated derivatives may be prepared by subjecting the caseino-macroglycopeptide obtained to a subsequent desialylation step, in which the oligosaccharide component of the macroglycopeptide is freed from sialic acids. To this end, the crude caseino-macroglycopeptide, which has not been purified beforehand by gel filtration, may be treated with an enzyme which specifically cleaves the sialic acid residues, for example a neuraminidase of *Clostridium perfringens*, after which the enzyme is thermally deactivated and the solution concentrated and dried, for example by freeze-drying.

The sialic acid residues may advantageously be cleaved by hydrolysis with a mineral acid in dilute aqueous solution, for example hydrochloric or sulfuric acid.

Irrespective of the desialylation method used, the crude products obtained are preferably purified as required by redissolution in water or by neutralization and gel filtration of the solution, followed by concentration and drying of the purified solution, for example by freeze-drying.

The caseino-glycopeptides may be prepared by subjecting the optionally desialylated caseino-macroglycopeptide to hydrolysis with a proteolytic enzyme.

Any proteolytic enzyme active at an acidic, neutral or alkaline pH may be used for this purpose. The enzyme may be of fungal origin, microbial origin (for example pronase, alcalase), vegetable origin (for example bromelin, ficin, papain) or animal origin (for example trypsin, pepsin, pancreatin). After the enzymatic treatment, the enzyme is deactivated, for example thermally, after which the solution is concentrated and dried, for example by freeze-drying, and the product obtained is preferably purified by redissolution in water, gel filtration and drying, for example freeze-drying.

The present invention also relates to a food, pharmaceutical or cosmetic composition incorporating the anti-plaque and anti-caries agent.

The agent may be incorporated in an amount effective in an article of confectionary, for example a sweet or chewing gum. It may be dissolved, for example in a sweetened beverage.

It may be used for disinfection of the buccal cavity and may be made up in, any form appropriate to that use, for example in an amount effective in the form of a tablet or lozenge for sucking, in the form of a soluble tablet or cube or, for example, in the form of an aqueous solution or emulsion as a mouthwash.

It may be incorporated in an amount effective in a toothpowder or toothpaste.

The anti-plaque and anti-caries agent may make up from 0.1 to 90% by weight of such a composition.

EXAMPLES

The invention is illustrated by the following Examples in which parts and percentages are by weight unless otherwise indicated.

EXAMPLES 1-6

1. An aqueous buffer solution of pH 6.3 is prepared from 5 g sodium caseinate of bovine origin and 100 ml water containing 10 mM sodium phosphate and 100 mM NaCl. To this solution is added 1 mg rennet (chymosine Sigma) dissolved beforehand in the buffer solution. After incubation for 1 h at 37° C., a 24% (weight/volume) solution of trichloroacetic acid (TCA) is slowly added with stirring to a final concentration of 12% TCA. A precipitate is formed and is separated by centrifugation, after which the supernatant phase is collected and dialyzed against pure water, the dialyzate being dried by freeze-drying. 0.8 g of crude bovine caseino-macroglycopeptide is obtained in this way.

2. 320 g of a powder-form concentrate of proteins from sweet whey of bovine origin are dissolved in 3.2 l water. The concentrate is obtained by ultrafiltration and diafiltration of sweet whey and contains 81% proteins, 1.3% lactose, 6.3% fats and 3.4% ash, based on the the weight of dry matter.

3.2 l of a 24% (weight/volume) solution of TCA are slowly added with stirring to this solution. A light precipitate is formed in suspension. After the suspension obtained has been left standing for 15 to 20 minutes, it is centrifuged at 3,000 r.p.m. for 15 minutes. The supernatant phase is recovered and extensively dialyzed against pure water to pH 5, concentrated to a volume of 500 ml, re-dialyzed against pure water, re-concentrated and dried by freeze-drying. 7.06 g of crude bovine caseino-macroglycopeptide are collected. After redissolution in a 0.1 M aqueous acetic acid solution and passage through a column of SEPHADEX G25, eluted with a 0.1 M aqueous acetic acid solution, followed by concentration and freeze-drying, 5.52 g of purified bovine caseino-macroglycopeptide are obtained.

3. 1 l skimmed goat's milk is acidified with an aqueous solution of 1 N hydrochloric acid to pH 4.65. The casein precipitates in the form of a fine suspension. The suspension is left standing overnight at 4° C. After centrifugation, the precipitate is collected and suspended in 500 ml water to which 1.7 g $CaCl_2$ dissolved in 10 ml water are then added with stirring. The mixture is then heated on a water bath to 35° C. and an aqueous solution of 1 N NaOH added to pH 6.8. The formation of a suspension is observed. A solution of 250 $\mu$l rennet in 5 ml water is slowly added to the suspension with slow stirring and, after stirring for 1 hour at 35° C., the pH is adjusted to 4.5 with an aqueous solution of HCl. After centrifugation, the precipitate is eliminated and a 24% (weight/volume) solution of TCA is added to the supernatant phase. The remaining procedure is then as described in Example 2. 0.25 g of crude caprine caseino-macroglycopeptide is collected. This compound may be purified by gel filtration (SEPHADEX G50) and eluted with a 0.1 M aqueous acetic acid solution to give 0.17 g of purified caprine caseino-macroglycopeptide.

4. Starting from 1 liter skimmed ewe's milk, the procedure described in Example 3 gives 0.37 g of crude ovine caseino-macroglycopeptide or 0.23 g of product purified by gel filtration.

5. Caprine whey emanating from the production of goat's cheese coagulated with rennet is collected immediately after production. 3.5 l of this whey are mixed with the same volume of a 24% (weight/volume) aqueous solution of TCA. The further procedure is then exactly as described in Example 2, giving 1.68 g crude caprine caseino-macroglycopeptide or 0.66 g of purified product after gel filtration as described in Example 3.

6. Starting from ovine whey, the procedure described in Example 5 gives 2.29 g of crude ovine caseino-macroglycopeptide or 1.44 g of purified product after gel filtration as described in Example 3.

EXAMPLES 7-10

7. 400 mg of the crude caseino-macroglycopeptide of Example are dissolved in 200 ml of a 50 mM aqueous solution of citrate/phosphate buffer at pH 5.40 units of neuraminidase of Clostridium perfringens (47 mg of type V, Sigma) are added to this solution which is then incubated for 1 hour at 37° C. After thermal denaturing of the enzyme, the solution is concentrated and dried by freeze-drying. After dissolution of the lyophilizate in 10 ml of a 10 mM buffer solution of acetic acid, the solution is subjected to gel filtration (SEPHADEX G50) with a 10 mM aqueous acetic acid solution. A pure, desialylated caseino-macroglycopeptide is obtained by concentration and freeze-drying.

8. 400 mg of the crude caseino-macroglycopeptide of Example 2 are subjected to acidic hydrolysis under controlled conditions either with 40 ml of a 10 mM aqueous HCl solution (for 2 h at 80° C.) or with 40 mM of a 25 mM aqueous $H_2SO_4$ solution (for 2 h at 80° C.). After cooling to ambient temperature, the solution is neutralized to pH 7 with an aqueous solution of 0.5 N NaOH, concentrated and freeze-dried. After the lyophilizate has been dissolved in a 0.1 M aqueous acetic acid solution, the solution is purified by gel filtration (SEPHADEX G25) with a 0.1 M aqueous acetic acid solution. After concentration and freeze-drying, a pure desialylated caseino-macroglycopeptide is obtained.

9. Starting from the crude caseino-macroglycopeptide of Example 3, the procedure described in Example 8 gives a desialylated caprine caseino-macroglycopeptide.

10. Starting from the crude caseino-macroglycopeptide of Example 4, the procedure described in Example 8 gives a desialylated ovine caseino-macroglycopeptide.

EXAMPLES 11-13

11. 2 g of the crude product of Example 2 are dissolved in 100 ml of an aqueous solution of Tris-HCl buffer (tris-(hydroxymethyl)-aminomethane, 50 mM, adjusted to pH 8.2 with an aqueous solution of 1 N HCl). After addition of 50 mg of Pronase E (Merck), the solution is incubated for 24 h at 40° C. in the presence of 5 ml toluene. Another 25 mg of Pronase E are added and the solution is incubated for 48 h at 40° C. After thermal inactivation of the enzyme, the solution is concentrated and dried by freeze-drying. The lyophilizate is dissolved in a 0.1 M aqueous acetic acid solution, after which the solution is subjected to gel filtration (SEPHADEX G50) and eluted with a 0.1 M aqueous acetic acid solution. After concentration and drying by freeze-drying, a pure bovine caseino-glycopeptide is obtained.

12. Proteolysis of the crude product of Example 8 in the same way as described in Example 11 gives a pure, desialylated bovine caseino-glycopeptide.

13. Proteolysis of the crude product of Example 4 in the same way as described in Example gives a pure ovine caseino-glycopeptide.

EXAMPLE 14-15

Strains and culture conditions

The following strains were used for testing the effect of the agents according to the invention:

One strain of *Actinomyces naeslundii* ATCC 12104.

Two strains of *Actinomyces viscosus* (OMZ 105 and OMZ 206), one strain of *Streptococcus sanguis* (OMZ 9) and one strain of *Streptococcus mutans* (OMZ 176) which come from Prof. Dr. B. Guggenheim, "Abteilung für Orale Mikrobiologie und Allgemeine Immunologie, Zahnärtztliches Institut, Universität Zürich, Schweiz (Department of Oral Microbiology and General Immunology, Dental Institute, University of Zurich, Switzerland)".

For the hemagglutination inhibition tests (Example 14), the *Actinomyces* strains (*A. naeslundii* ATCC 12104 and *A. viscosus* OMZ 105) were cultured in a commercial medium ("Actinomyces broth" BBL, Becton, Dickinson & Co., or Difco Laboratories). For the tests conducted without control of the bacterial growth phase (Table I), this medium was completed by the addition of sodium thioglycolate (0.05%) and the bacteria were harvested after a single passage. For the tests carried out with a strain harvested in the exponential growth phase (Table II), a first passage of 24 h being followed by a second passage of 16 h, on both occasions in the above non-completed medium.

For the tests to determine the inhibition of adhesion to the surface of plastic material (Example 15), the strains of *A. viscosus* (OMZ 105 and OMZ 206) were cultured for 36 h in the same medium (non-completed). The Strepococcus strains (*S. sanguis* OMZ 9 and *S. mutans* OMZ 176) were cultured for 24 h in another commercial medium ("Brain-Heart Infusion", Difco) completed by glucose (0.5%).

14. Inhibition of hemagglutination caused by Actinomyces strains in the presence of kappa-caseino-glycopeptide and derivatives thereof After harvesting, the bacteria were washed with salt water (0.9% NaCl) and the suspensions adjusted to an optical density (OD) of 8.

The human erythrocytes (gr. AR+) were desialylated with neuraminidase from *Vibrio cholera* (Behring) just before they were used in the tests. After several washes, they were suspended in a concentration of 1% in salt water already containing 1% methyl α-mannoside.

Estimation of the hemagglutinating titer

In a "Micro-Titre" plate, 50 µl portions of the bacterial suspensions described above, grouped into 2 to 2 dilution series, were mixed with portions (50 µl) of the suspension of desialylated erythrocytes likewise described above. The readings were made after immobilization for 1 hour at ambient temperature.

Hemagglutination inhibition tests

These tests were carried out by mixing 25 µl of the bacterial suspension corresponding to four hemagglutinating doses (titer determined by the above test), 50 µl of the erythrocyte suspension already described and 25 µl of a saline solution containing series of 2 to 2 dilutions of the various inhibitors. When necessary, the pH of the suspensions of inhibitors was adjusted before mixing to pH 7 with an aqueous solution of 0.5 N NaOH. The readings were made after immobilization for 1 hour at ambient temperature. The results are shown in Tables I and II below:

TABLE I

| Inhibition of hemagglutination of desialylated human erythrocytes (A+) | | |
|---|---|---|
| | Concentration[a] (mg/l) | |
| Product | *A. viscosus* OMZ 105 | *A. naeslundii* ATCC 12104 |
| Example 2 | 0.63 | 1.25 |
| Example 8 | 0.94 | 1.88 |
| Example 11 | 5 | 10 |
| Example 12 | 2.5 | 5 |
| Example 4 | 4.75 | 9.5 |
| Example 10 | 1.13 | 2.25 |
| Example 13 | 1.88 | 3.75 |
| Example 3 | 1.75 | 3.5 |
| Example 9 | 1.25 | 2.5 |
| Lactose (for comparison) | none[b] | none[b] |

Legend:
[a] Minimum concentration resulting in complete inhibition of hemagglutination.
[b] No inhibition up to 20 mg/ml.

TABLE II

| Inhibition of hemagglutination of desialylated human erythrocytes (A+) by *A. viscosus* OMZ (harvested in the exponential phase) | | | |
|---|---|---|---|
| | Concentration[a] (mg/ml) | | Activity relative to |
| Product | Expressed in dry weight/ml | Expressed in galactoside equivalents/ml | Example 12 as reference (x times) |
| Example 2 | 5 | 0.36 | 3 |
| Example 8 | 0.075 | 0.008 | 120 |
| Example 11 | 15 | 2.12 | 0.5 |
| Example 12 | 4.5 | 0.97 | 1 |
| Example 6 | none[b] | >0.34 | — |

TABLE II-continued

Inhibition of hemagglutination of desialylated human erythrocytes (A+) by *A.viscosus* OMZ (harvested in the exponential phase)

| Product | Concentration$^{(a)}$ (mg/ml) Expressed in dry weight/ml | Concentration$^{(a)}$ (mg/ml) Expressed in galactoside equivalents/ml | Activity relative to Example 12 as reference (x times) |
|---|---|---|---|
| Example 10 | 5 | 0.23 | 4 |
| Example 5 | none$^{(b)}$ | >1.46 | — |
| Lactose (for comparison) | none$^{(b)}$ | >10 | — |

Legend: cf. TABLE I

It can be seen from the foregoing results that the various agents according to the invention are very strong inhibitors of the hemagglutinations governed by type 2 pili. Table II shows particularly clearly the very high activity of desialylated bovine caseino-macroglycopeptide (of Example 8). Under the conditions used for the tests, the known inhibitor of bacterial adhesion governed by these pili (lactose) is completely ineffective here.

15. Inhibition of the adhesion of strains of *A. viscosus*, *S. sanguis* and *S. mutans* to a surface of plastic material in the presence of bovine kappa-caseino-glycopeptides and derivatives thereof After harvesting, the bacteria were washed with an aqueous buffer solution (0.9% NaCl, 1 mM Tris, 0.1 mM CaCl$_2$, 0.1 mM MgCl$_2$, 0.02% NaN$_3$) and the suspensions were adjusted to an OD of 0.4. In the case of *A. viscosus* OMZ 206, the suspension had to be re-adjusted to an OD of 0.4 after 6 hours' growth in the above buffer solution. 1 ml portions of these bacterial suspensions were decanted into polypropylene tubes containing or not containing the various compounds to be evaluated. The suspensions were then stirred for 10 s every hour. After 4 h and in each case, the OD of the resulting suspension was measured after decantation. The difference between the original and residual OD was finally related to the OD of the starting suspension (% adhesion). The ratio between the results obtained in the presence of and absence of inhibitor enabled the percentage inhibition to be calculated in each case. The results are set out in Tables III and IV below.

TABLE III

Adhesion and inhibition of bacterial adhesion to plastic tubes

| Product | S. sanguis OMZ 9$^{(a)}$ | S. mutans OMZ 176 | A. viscosus OMZ 105$^{(a)}$ | A. viscosus OMZ 206 |
|---|---|---|---|---|
| | Adhesion (%) | | | |
| None (control) | 90 | 71 | 43 | 37 |
| | Inhibition (%) | | | |
| Example 2 (1 mg/ml)$^{(b)}$ | 86 | 83 | 93 | 86 |
| Example 8 (1 mg/ml)$^{(b)}$ | 97 | 80 | 100 | 78 |
| Lactose (1 mg/ml)$^{(b)}$ | 12 | 4 | 14 | 15 |
| Galactose (1 mg/ml)$^{(b)}$ | 12 | 4 | 12 | n.t.$^{(c)}$ |
| Methyl α annoside | 11 | 3 | 10 | n.t. |
| Polyglutamic acid (1 mg/ml) | 6 | 20 | 22 | n.t. |
| Polylysine (1 mg/ml) | 12 | 30 | 46 | n.t. |

$^{(a)}$In the case of these two strains, preliminary tests had shown the specificity of the inhibitory effect of the caseino-macroglycopeptides and their desialylated bovine derivatives in relation to the non-activity of glucose and glycine in such an experimental system.
$^{(b)}$With each of the four strains, other tests have shown that this inhibitory effect of the caseino-macroglyco-peptides and their desialylated bovine derivatives is not impaired by the presence of variable concentrations (0.05, 0.1, 0.2 and 0.5%) of edible sugars (glucose, sucrose, starch and fructose).
$^{(c)}$n.t. = not tested.

TABLE IV

Inhibition of the adhesion of *S. sanguis* OMZ 9 and of *S. mutans* OMZ 176 to plastic tubes in a concentration of 100 μg/ml

| Product | Inhibition % S. sanguis OMZ 9 | Inhibition % S. mutans OMZ 176 |
|---|---|---|
| Example 2 | 61 | 65 |
| Example 8 | 69 | 69 |
| Example 11 | 24 | 23 |
| Example 12 | 24 | 44 |

The foregoing results show that the agents according to the invention are active against adhesion to the surface of a plastic material which concerns the Streptococci strains as much as the Actinomyces strain. An experimental model such as this is representative of the situation prevailing in the buccal cavity.

By way of comparison, lactose and galactose in no way show the same levels of activity.

I claim:

1. A composition in a form for treating and inhibiting formation of dental plaque and caries in a buccal cavity comprising a carrier selected from a group of carriers consisting of a chewing gum, a lozenge for sucking, a mouthwash, a tooth powder and a toothpaste containing an active principle which is obtained from material of lactic origin selected from a group consisting of kappa-caseino-glycopeptides and desialylated derivatives thereof and which is in an amount effective for treating bacteria and for inhibiting adhesion of bacteria in the buccal cavity which are responsible for formation of dental plaque and caries in the buccal cavity.

2. A composition according to claim 1 wherein the composition contains the active principle in an amount of from 0.1% to 90% by weight.

3. A composition according to claim 1 wherein the active principle is selected from a group consisting of bovine, ovine and caprine caseino-macroglycopeptides and desialylated derivates of the bovine, ovine and caprine caseino-macroglycopeptides.

4. A composition according to claim 1 wherein the active principle is a desialylated bovine caseino-macroglycopeptide.

5. A composition according to claim 1 wherein the active principle has been obtained from a fraction of a concentrate of lactic proteins, which is non-precipitable with trichloroacetic acid, emanating from ultrafiltration and diafiltration of bovine sweet whey.

6. A composition according to claim 5 wherein the active principle has been purified by gel filtration.

* * * * *

Disclaimer 4,994,441—*Jean-Richard Neeser,* Lausanne, Switzerland. DENTAL ANTI-PLAQUE AND ANTI-CARIES AGENT. Patent dated Feb. 19, 1991. Disclaimer filed Nov. 19, 1990. by the assignee, Nestec S.A.

The term of this patent subsequent to Feb. 12, 2008, has been disclaimed.
[ *Official Gazette June 11, 1991* ]